US00PP12564P2

(12) United States Plant Patent
Vandenberg

(10) Patent No.: US PP12,564 P2
(45) Date of Patent: Apr. 23, 2002

(54) CHRYSANTHEMUM PLANT NAMED 'COPPER YOGILROY'

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 31 days.

(21) Appl. No.: 09/594,760

(22) Filed: Jun. 16, 2000

(51) Int. Cl.[7] ..... A01H 5/00
(52) U.S. Cl. ..... Plt./290
(58) Field of Search ..... Plt./287, 290

(56) References Cited

PUBLICATIONS

UPOC–ROM, 2001/03, Plant Variety Database, GTI Jouve Retrieval Software, citation for 'Copper Yogilroy'.

*Primary Examiner*—Howard J. Locker
(74) *Attorney, Agent, or Firm*—C. A. Whealy

(57) ABSTRACT

A distinct cultivar of Chrysanthemum plant named 'Copper Yogilroy', characterized by its upright, outwardly spreading, compact and uniformly mounded plant habit; uniform flowering response; early flowering, eight-week response time; large formal decorative-type inflorescences that are about 9.9 cm in diameter; warm medium bronze-colored ray florets; and good postproduction longevity with inflorescences maintaining good substance and color for about three or four weeks in an interior environment.

1 Drawing Sheet

BACKGROUND OF THE INVENTION

The present Invention relates to a new and distinct cultivar of Chrysanthemum plant, botanically known as *Dendranthema grandiflora* and hereinafter referred to by the cultivar name Copper Yogilroy.

The new Chrysanthemum is a product of a mutation induction breeding program conducted by the Inventor in Fort Myers, Fla., and Salinas, Calif. The objective of the program is to create new Chrysanthemum cultivars with desirable inflorescence form and floret colors and good postproduction longevity.

The new Chrysanthemum originated by exposing unrooted cuttings of the Chrysanthemum cultivar Amber Yogilroy, not patented, to X-ray radiation in January, 1997, in Fort Myers, Fla. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Salinas, Calif. The new Chrysanthemem was discovered and selected by the Inventor as a single flowering plant within this population in August, 1997. The selection of this plant was based on its desirable inflorescence form and ray floret color.

Asexual reproduction of the new Chrysanthemum by vegetative tip cuttings was first conducted in Salinas, Calif. in November, 1997. Asexual reproduction by cuttings has shown that the unique features this new Chrysanthemum are stable and reproduced true to type in successive generations.

SUMMARY OF THE INVENTION

The cultivar Copper Yogilroy has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Copper Yogilroy'. These characteristics in combination distinguish 'Copper Yogilroy' as a new and distinct Chrysanthemum:

1. Upright, outwardly spreading, compact and uniformly mounded plant habit.

2. Dense, full plants.

3. Uniform flowering response.

4. Early flowering, eight-week response time.

5. Large formal decorative-type inflorescences that are about 9.9 cm in diameter.

6. Warm medium bronze-colored ray florets.

7. Good postproduction longevity with inflorescences maintaining good substance and color for about three or four weeks in an interior environment.

Plants of the new Chrysanthemum differ from plants of the parent cultivar Amber Yogilroy and the cultivar Yellow Yogilroy (U.S. Plant patent application Ser. No. 09/594,761 filed concurrently with this application) primarily in ray floret color.

Plants of the new Chrysanthemum differ from plants of the cultivar, Gilroy, disclosed in U.S. Plant Pat. No. 10,252, in the following characteristics:

1. Plants of the new Chrysanthemum are slightly less vigorous and shorter than plants of the cultivar Gilroy.

2. Ray floret color of plants of the new Chrysanthemum is darker bronze than ray floret color of plants of the cultivar Gilroy.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical desription which more accurately describe the actual colors of the new Chrysanthemum.

The photograph at the top of the sheet comprises a top perspective view of a typical flowering plant of 'Copper Yogilroy'.

The photograph at the bottom of the sheet comprises a close-up view of typical inflorescences of the cultivar Copper Yogilroy.

DETAILED BOTANICAL DESCRIPTION

In the following description, color references are made to The Royal Horticultural Society Colour Chart except where general terms of ordinary dictionary significance are used. The following observations and measurements describe plants grown and flowered during the Spring in Salinas, Calif. and Leamington, Ontario, Canada, under greenhouse conditions which approximate those generally used in commercial potted Chrysanthemum production. Four unrooted cuttings were directly stuck in a 15-cm container and pinched once. Plants used for this description were grown as disbud-types. Measurements and numerical values represent averages of typical flowering plants.

Botanical classification: *Dendranthema grandiflora* cultivar Copper Yogilroy.

Commercial classification: Decorative-type potted Chrysanthemum.

Parentage: Induced mutation of *Dendranthema grandiflora* cultivar Amber Yogilroy, not patented.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous decorative-type potted Chrysanthemum typically grown as a disbud-type. Compact; inverted traingle; stems upright and outwardly spreading giving a uniformly mounded appearance to the plant. About three lateral branches develop after removal of terminal apex (pinching); full and dense plants. Moderate vigor.

*Plant height.*—About 19 cm.

*Plant width.*—About 33 cm.

*Lateral branches.*—Length: About 12 cm. Diameter: About 3.5 mm. Internode length: About 1.4 cm. Strength: Flexible, but strong. Texture: Pubescent. Color: 144A.

*Foliage description.*—Arrangement: Alternate. Length: About 6.7 cm. Width: About 4.8 cm. Apex: Mucronate. Base: Mostly attenuate. Margin: Palmately lobed, sinuses between lateral lobes mostly divergent, occasionally parallel. Texture: Upper and lower surfaces with very fine pubescence; veins prominent on lower surface. Color: Young foliage upper surface: 147A. Young foliage lower surface: 147B. Mature foliage upper surface: 147A. Mature foliage lower surface: 147B. Venation upper surface: 147A to 147B. Venation lower surface: 147B. Petiole length: About 2.2 cm. Petiole diameter: About 2.5 mm. Petiole color: 147B.

Inflorescence description:

*Appearance.*—Formal decorative-type inflorescence form with elongated oblong-shaped ray florets. Inflorescences borne on terminals above foliage. Disk and ray florets arranged acropetally on a capitulum. Not fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about eight weeks later; early flowering.

*Postproduction longevity.*—Inflorescences maintain good color and substance for about three or four weeks in an interior environment.

*Quantity of inflorescences.*—Typically grown as a disbud-type with one inflorescence per lateral stem; about three inflorescences per plant.

*Inflorescence bud.*—Height: About 7 mm. Diameter: About 8 mm. Color: Close to 143A.

*Inflorescence size.*—Diameter: About 9.9 cm. Depth (height): About 3.1 cm. Diameter of disc: Less than 2 mm, inconspicuous. Receptacle diameter: About 7 mm.

*Ray florets.*—Shape: Elongated-oblong. Orientation: Initially incurved, outer rows opening to perpendicular to stem or reflexed. Aspect: Initially concave then becoming convex with development. Length: About 5.3 cm. Width: About 1.2 cm. Apex: Mostly rounded, some emarginate, mammilate or dentate. Base: Attenuate; short to medium corolla tube. Margin: Entire. Texture: Smooth, glabrous, satiny. Number of ray florets per inflorescence: About 180. Color: When opening: Close to 171A to 171B to close to 167A. Fully opened, upper surface: Yellow, 9A, overlain with red, close to 45A. Tonality, close to 169A; with development, to 164A to close to 167A. Fully opened, lower surface: Yellow, 9B to 9C faintly overlain with dark red, close to 53A. Tonality, close to 164B to 164D with red undertones.

*Disc florets.*—Shape: Tubular, flared. Apex: Five-pointed. Length: About 6 mm. Width: Apex, about 1.5 mm; base, about 1 mm. Number of disc florets per inflorescence: Less than 10; inconspicuous. Color: Immature: 144A. Mature: Apex: 5A. Mid-section and base: White, 155D.

*Reproductive organs.*—Androecium: Present on disc florets only. Anther color: 9A. Pollen amount: None observed. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Copper Yogilroy', as illustrated and described.

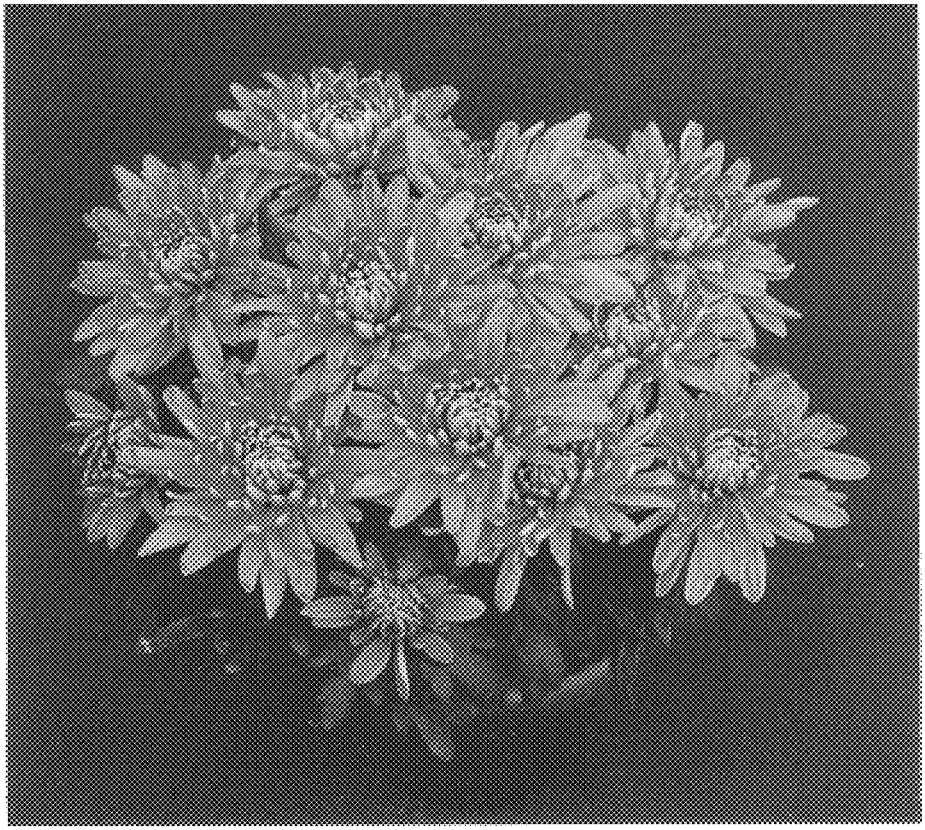
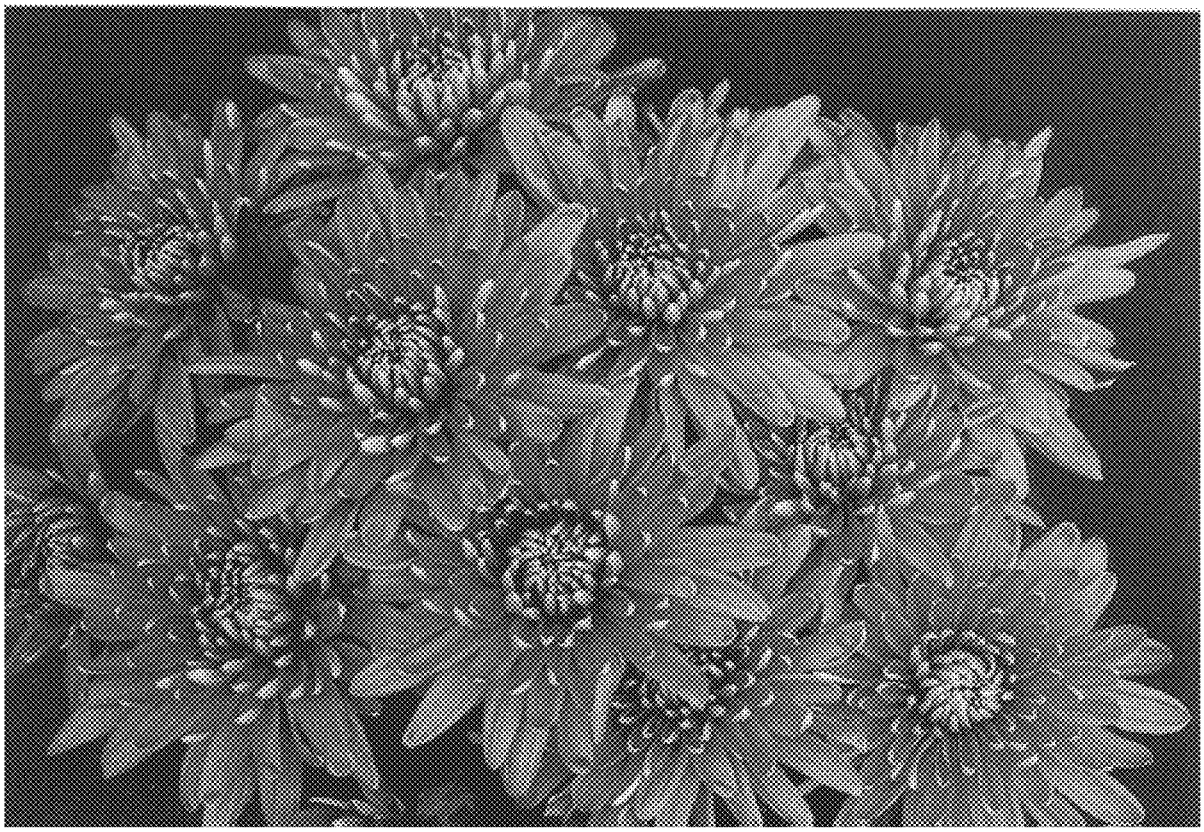

* * * * *